United States Patent [19]

Parravicini

[11] 4,352,211

[45] Oct. 5, 1982

[54] CARDIAC VALVE PROSTHESIS

[76] Inventor: Roberto Parravicini, Corso Genova, 13, 20100 Milan, Italy

[21] Appl. No.: 224,297

[22] Filed: Jan. 12, 1981

[30] Foreign Application Priority Data

Jan. 16, 1980 [IT] Italy ................................ 19242 A/80

[51] Int. Cl.³ ................................................ A61F 1/22
[52] U.S. Cl. ...................................... 3/1.5; 137/527; 137/527.8
[58] Field of Search .................. 3/1.5; 137/527.8, 527

[56] References Cited

U.S. PATENT DOCUMENTS

| | | | |
|---|---|---|---|
| 3,538,514 | 11/1970 | Schimert et al. | 3/1.5 |
| 4,159,543 | 7/1979 | Carpentier | 3/1.5 |
| 4,178,638 | 12/1979 | Meyer | 3/1.5 |
| 4,178,639 | 12/1979 | Bokros | 3/1.5 |

Primary Examiner—Ronald L. Frinks
Attorney, Agent, or Firm—Bucknam and Archer

[57] ABSTRACT

An artificial cardiac valve of the type comprising a plastic material ring member (1) effective to act as a valve seat, encompassed by a plastic cloth outside ring (3) effective to act as an anchoring member for the yarns tying the cardiac valve to the host tissue. The valve is provided with a shutter member (4,4a) formed by two arcuate valves (4,4a) each provided at the central zone of the edge provided for resting on the valve seat ring (1) with two thin lugs (5). The valve seat ring (1) is provided with seats (9,9') formed in the walls thereof at diametrically opposed positions, effective to freely receive the lugs (5). The valve is particularly useful as an aortic or mitral valve.

4 Claims, 9 Drawing Figures

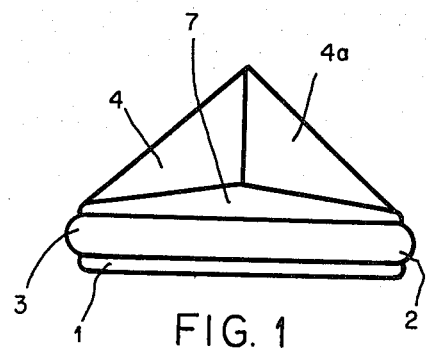
FIG. 1
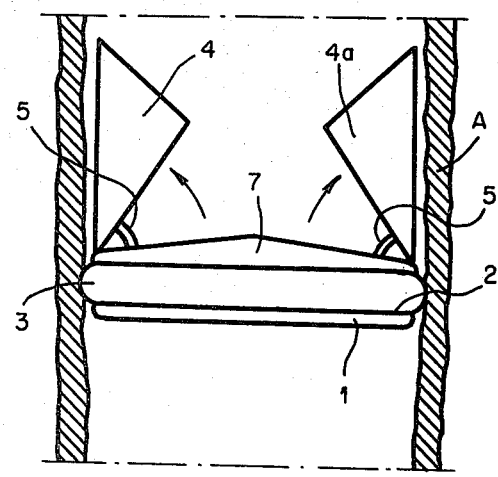
FIG. 2
FIG. 3
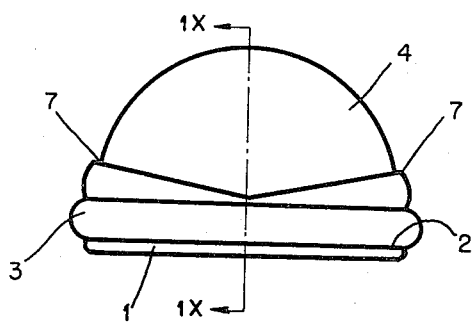
FIG. 4
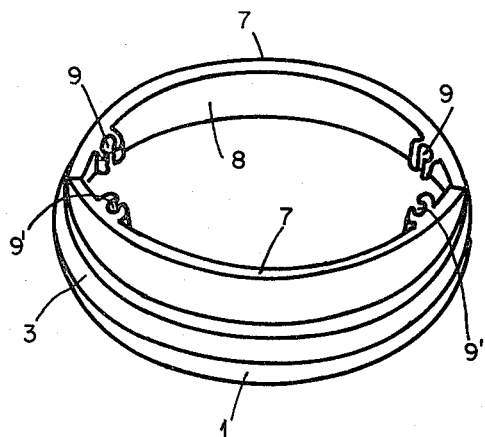

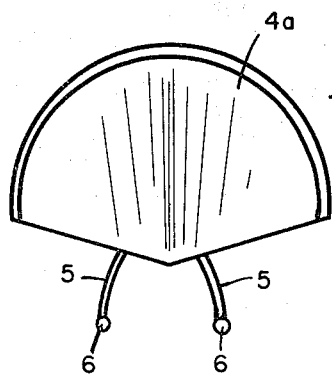
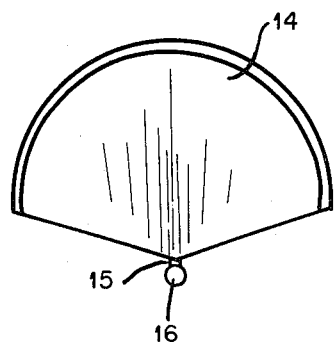
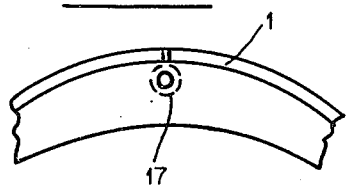
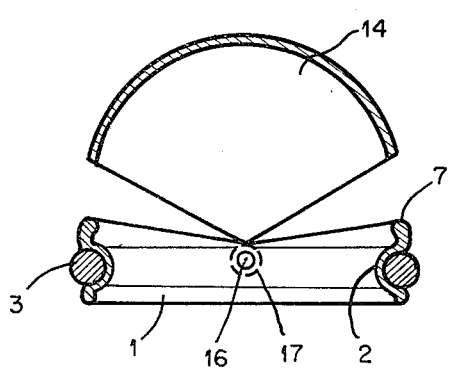
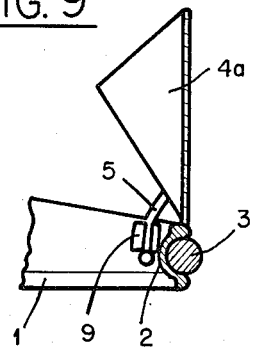

CARDIAC VALVE PROSTHESIS

BACKGROUND OF THE INVENTION

The present invention relates to the cardiac valve prostheses, also called "cardiac mechanical prostheses", since they are effective to provide the operation of the cardiac valves, while being of different anatomic construction.

As it is known, the surgery of the cardiac valve diseases only rarely adopts conservative methods, since, very frequently, the cardiac valve lesions are so serious that they require a complete extirpation of the sick cardiac valve apparatus, to be replaced with artificial valves.

The main and most important features that an artificial cardiac valve must have to approach as far as possible an ideal cardiac valve are: (a) a nearly unlimited duration (b) a perfect acceptance by the host and/or hostess, in particular by the endocardic tissues whereof, (c) a hemodynamic function, that is a circulation function, as far as possible equal to that of a normal cardiac valve, with respect to the facility of installation.

In this field, intensive researches have been made for finding such a cardiac valve effective to satisfactorily meet the thereinabove stated requirements.

One of these valves is the Starr valve, which consists of a Teflon ring supporting a metal cage in the inside whereof a ball is located.

This ring acts as a valve seat, the ball as a shutter and the cage as a guide for the ball stroke. Thus, the Starr valve can be considered as a conventional ball valve as those used in the fluid dynamic field.

Another artificial cardiac valve which has given good results, consists of a special plastic material ring, well compatible with the endocardiac tissue, and acting as a valve seat provided on the outside thereof with a peripheral groove effective to receive or house a ring member also made of a special plastic material cloth and provided for acting as an anchoring member for tying yarns as applied to the host tissue. The valve seat forming ring is provided with two small and thin lugs, projected to the inside and effective to engage with two arms rigid with a plate member effective to act as a valve shutter and to provide a loose pivoting coupling.

In this case, the cardiac valve can be considered as a conventional hinge valve, as used in the industry, and it eliminates the drawback related to the fixing of the cage member of the Starr valve.

However, these artificial valves are not devoid of drawbacks. More specifically, they compel the man/-woman thereto the valve is fitted to submit to a daily anticoagulating treatment to reduce to a minimum the possibility of fibrinous deposits or coagula on the artificial valve structures, particularly those which are located in the blood stream and which are engaged thereby. For example, in the Starr valve, these structures consist of the metal cage and the ball and, in the hinge type of valve, they consist of the lugs and pivoting arms of the plate member.

The fibrinous deposits or coagula, in time, either because of mechanical effects of the ball or pivoting lugs or due to other reasons, can cause the detachement of valve portions which, as conveyed by the blood stream, can be brought towards the peripheric arteries, thereby causing embolisms to occur, which are sometimes very serious, especially if the embolus locates in the brain.

The hinged plate type of valve, though it has the feature of determining smaller fibrinous deposits or coagula, due to the smaller surface exposed to the blood stream, presents however the drawback that, in time, since the opening of the plate member is restrained by the lugs and the arms, it is not effectively complete and becomes smaller and smaller, due to the aforesaid deposits, thereby a narrowing of the blood flow rate through the valve occurs, with a consequent stanching of the blood in the cardiac cavities and possible cardiac decompensation.

SUMMARY OF THE INVENTION

Thus, the present invention sets out to provide an artificial cardiac valve, of the mechanical type, and of new design, effective to eliminate as far as possible the drawbacks of the fibrinous deposits and coagula of the known cardiac valves, by reducing to a minimum the valve portions exposed to the blood stream originating said deposits, while allowing for the cardiac valve to completely open and eliminating a narrowing or reducing of the blood flow rate.

More specifically, the artificial cardiac valve according to the present invention, of the type provided with a ring member effective to act as a valve seat, encompassed by a plastic material ring member effective to act as an anchoring member for tying the cardiac valve to the host tissue, is characterized in that two arcuated valve members are provided effective to act as a shutter, each said arcuated valve members being provided, at the central zone of the edge thereof provided for resting on the valve seat forming ring member, with a thin lug, the valve seat forming ring member being provided with seats formed on the wall thereof at diametrically opposite positions the lugs being effective to be inserted into the seats in such a way as to be able to freely move to expose a very small surface to the blood stream, thereby reducing to a minimum the fibrinous sediments and the coagula while allowing for the valve to completely open to prevent the blood stream from being narrowed.

According to a feature of the present invention, the pivoting lugs are two for each half valve the pivoting lugs being spaced one from another, and the valve seat forming ring is provided two seat pluralities each having two seats, as diametrically oppositely located at the pivoting lugs, in order to satisfactorily guide or drive the opening and closing strokes of the two valve portions or valves forming the valve shutter as the lugs are inserted into the related seats.

BRIEF DESCRIPTION OF THE DRAWINGS

The invention will be described thereinafter in a more detailed way with reference to two embodiments thereof, given by way of an indicative and not limitative example, being illustrated in the accompanying drawings, where:

FIG. 1 is a side elevation view of the artificial cardiac valve according to the present invention, the valve members being in the closed position;

FIG. 2 is a side elevation view of the valve of FIG. 1, the valve members being in the open position and inserted into the aorta, shown in cross-section;

FIG. 3 is an elevation view of that same valve of FIG. 1, as seen from the left side;

FIG. 4 is a perspective view of the ring member forming the seat of the valve and provided, on the outside periphery, with the plastic material ring member provided for anchoring the aorta tying yarns, and showing two pluralities of diametrically opposite seats, effective to house the valve pivoting lugs;

FIG. 5 is a front elevation view showing one of the valve portions forming the shutter of the valve, provided with two thin pivoting lugs, effective to engage with the seats formed in the ring member of FIG. 4;

FIG. 6 is a front elevation view illustrating one of the two portions or "valves" of the the valve shutter, as provided with a single pivoting lug;

FIG. 7 illustrates a portion of the valve seat forming ring member, as provided with a pivoting seat effective to house the lug of the valve portion shown in FIG. 6;

FIG. 8 is a cross-section of the valve, in the open position thereof, as shown in FIGS. 6 and 7, taken along the perimetrical line perpendicular to that passing through the two pivoting seats; and FIG. 9 is a partial cross-section of the valve in the open position thereof, as shown in FIGS. 1 to 5, taken substantially along the line IX—IX of FIG. 3.

Referring now to the drawings, and more specifically to FIGS. 1 to 5 and 9, a first embodiment of the invention is herein illustrated. The artificial cardiac valve herein illustrated consists, essentially, of a rigid plastic material ring member 1, compatible with the connective tissue to which the ring member is to be fixed, which, in this case is indicated in FIG. 2 as the aorta A A plastic material which is well suited for this application is that commercially available with the trademark Pyrolite which has the properties of being effective to be sterilized in an autoclave, is compatible with the tissues, has a long duration, is resistant against the attack of the chemicals required for this type of prosthesis.

The rigid plastic material ring member 1, forming the valve seat, is provided with an outside peripheral groove 2 in which a plastic cloth material ring member 3 is inserted. A plastic fibrous material well suited for this application is that commercially available with the trademark DACRON having the properties of being resistant against the organic liquids, chemically and biologically inert, mechanically resistant and effective to be sterilized in an autoclave, as required for this type of cloth materials.

The members described hereinabove are the fixed members of the valve.

The movable members consist of two valve portions or "valves" 4,4a of arcuated shape, and having, in plan, the form of an obtuse-angled circular sector (FIG. 5).

The valve portions 4,4a are provided, along their edge provided for engaging with the ring member 1, with two thin lugs 5, terminating with a ball point portions 6.

The valve seat forming ring, between the edge provided for engaging with the valve portions 4,4a, is formed by two cuspidated portions 7, serving to facilitate the opening movement of said valves 4,4a.

Furthermore, on the inner wall 8 of the ring member 1, there are provided two pluralities of diametrically opposite seats 9,9', formed by projecting arcuated collapsible tabs, effective to house the thin lugs 5 and hold the lugs therein with a clearance to permit the lugs to freely move. Upon having snap inserted the lugs 5, the valve 4,4a will be hinged to the ring member 1 and thus their opening and closing movements will be guided in two portions, thereby preventing the valves from laterally moving.

Owing to the very small surface of the pivoting zone exposed to the blood stream, it is possible to have in these zones a great reduction of the fibrinous material deposits and coagula and hence of the possible embolus formation.

The embodiments illustrated in FIGS. 6 and 7 differs from the embodiment illustrated hereinabove only due to the fact that the valve portions 14 are provided, at the center of the edge provided for engaging with the valve seat forming ring 1, with a single lug 15, of very reduced length, also terminating with a ball-shaped point portion 16.

In this case, on the inner wall of the ring member 1, there are formed two spherical seats 17, diametrically opposite, communicating with the outside of the edge of the ring 1 and provided for snap receiving the spherical pointed portions 16 of the lug 15, with a clearance, to permit the valve to freely move.

According to this embodiment, the surface of the pivoting zone exposed to the blood stream is nearly zero and accordingly the deposit of fibrinous materials and coagula, and hence the possibility of embolus formation, is reduced to a minimum.

From the above description it should be clear that an improved artificial cardiac valve has been provided which, in addition to having great advantages from the constructional and assemblying point of view, has the important feature of reducing to a minimum the possibility of the formation of fibrinous material deposits or coagula, with a self-evident reduction of the possibility of embolus formation, which is very dangerous for the man/woman bearing the valve.

Furthermore, the artificial cardiac valve according to the present invention affords a full opening of the passage port, thereof, thereby its hemodynamic function is almost equal to that of a normal cardiac valve: thus any possibility of narrowing the blood flow rate through the valve is eliminated with the great advantage that, frequently, as the instant valve is applied to a patient, his/her heart remarkably reduces its volume (in fact the cardiac hypertrophy is due to the increase of the work to which the heart is subjected because of valve lesions or cardiac diseases in general), improves its contractility and the cardiac decompensation status disappears.

Obviously the artificial cardiac valve according to the present invention is not limited to the thereinabove described and illustrated embodiments thereof and it is susceptible to all of the variations and modifications falling within the scope of the accompanying claims and not departing from the inventive idea.

I claim:

1. An artificial cardiac valve which comprises a first ring member (1) capable of acting as a valve seat, a second plastic material ring member (3) encompassing the first ring member and acting as an anchoring member for tying the cardiac valve to the host tissue, two arcuated valve members (4, 4a) capable of acting as a shutter, each arcuated valve member being provided in the center of its edge with a lug (5, 15), said lug being integral with each of said valve members and having a ball-point portion (6, 16) at the end thereof, said first ring member (1) being provided with seats on the inner wall thereof at diametrically opposite positions, said lug being insertable into said seats with a clearance sufficient to permit free movement of the lug.

2. The cardiac valve, according to claim 1 wherein each of said valve members is provided with two lugs spaced one from the other and provided with ball-point portions, and said first ring member (1) is provided with two pluralities of seats, said seats being diametrically opposite to each other.

3. An artificial cardiac valve, according to claim 1 or 2 wherein each said seat formed in the inner wall of said first ring member (1) consists of two inwardly bent tabs providing a port having a diameter greater than said lug diameter to allow for said lugs to freely move as they are inserted thereinto.

4. An artificial cardiac valve, according to claim 1 or 2 wherein said seats consist of substantially spherical cavities for snap engagement with the ball-point portions of said lugs.

* * * * *